(12) United States Patent
Owens et al.

(10) Patent No.: US 8,835,394 B2
(45) Date of Patent: *Sep. 16, 2014

(54) TREATMENT FOR BASAL CELL CARCINOMA

(75) Inventors: Mary L. Owens, Cottage Grove, MN (US); Terrance L. Fox, Oakdale, MN (US); Angela M. Ginkel, St. Paul, MN (US)

(73) Assignee: Medicis Pharmaceutical Corporation, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/276,068

(22) Filed: Oct. 18, 2011

(65) Prior Publication Data

US 2012/0035205 A1    Feb. 9, 2012

Related U.S. Application Data

(63) Continuation of application No. 12/798,356, filed on Apr. 2, 2010, now abandoned, which is a continuation of application No. 12/008,961, filed on Jan. 15, 2008, now Pat. No. 7,696,159, which is a continuation of application No. 10/808,004, filed on Mar. 24, 2004, now abandoned.

(60) Provisional application No. 60/457,265, filed on Mar. 25, 2003.

(51) Int. Cl.
*A61K 38/00* (2006.01)
*A61K 31/70* (2006.01)
*A01N 57/00* (2006.01)

(52) U.S. Cl.
USPC .................. 514/19.3; 514/43; 514/91

(58) Field of Classification Search
None
See application file for complete search history.

(56) References Cited

U.S. PATENT DOCUMENTS

| | | |
|---|---|---|
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,376,501 A | 12/1994 | Mariën et al. |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,605,899 A | 2/1997 | Gerster et al. |
| 5,693,811 A | 12/1997 | Lindstrom |
| 5,741,908 A | 4/1998 | Gerster et al. |
| 5,756,747 A | 5/1998 | Gerster |
| 5,939,090 A | 8/1999 | Beaurline et al. |
| 6,028,076 A | 2/2000 | Hirota et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,113,918 A | 9/2000 | Johnson et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,303,347 B1 | 10/2001 | Johnson et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,376,501 B1 | 4/2002 | Isobe et al. |
| 6,376,669 B1 | 4/2002 | Rice et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,810 B1 | 9/2002 | Coleman et al. |

(Continued)

FOREIGN PATENT DOCUMENTS

| | | |
|---|---|---|
| EP | 0 394 026 | 10/1990 |
| EP | 1 104 764 A1 | 6/2001 |

(Continued)

OTHER PUBLICATIONS

Beutner, 1999, J. Am. Acad. Dermatol., vol. 41, pp. 1002-1007.*

(Continued)

*Primary Examiner* — Joanne Hama
*Assistant Examiner* — Ian Dang
(74) *Attorney, Agent, or Firm* — Kilpatrick Townsend & Stockton LLP

(57) ABSTRACT

The present invention provides a method of treating basal cell carcinoma in a subject. Generally, the method includes administering to the subject an amount of IRM compound effective for treating basal cell carcinoma in a treatment cycle that includes at least two consecutive days in which the IRM compound is administered and at least one day in which the IRM compound is not administered.

12 Claims, 3 Drawing Sheets

(56) References Cited

U.S. PATENT DOCUMENTS

| | | |
|---|---|---|
| 6,476,000 B1 | 11/2002 | Agrawal |
| 6,514,985 B1 | 2/2003 | Gerster et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0199461 A1 | 10/2003 | Averett et al. |
| 2004/0010007 A1 | 1/2004 | Dellaria et al. |

FOREIGN PATENT DOCUMENTS

| | | |
|---|---|---|
| JP | 9208584 | 8/1997 |
| JP | 11-80156 | 3/1999 |
| JP | 11080156 | 3/1999 |
| JP | 11-222432 | 8/1999 |
| JP | 11 222432 | 8/1999 |
| JP | 2000-247884 | 9/2000 |
| WO | WO 00/47719 A2 | 8/2000 |
| WO | WO 00/75304 A1 | 12/2000 |
| WO | WO 00/76518 A1 | 12/2000 |
| WO | WO 00/78505 A1 | 12/2000 |
| WO | WO 01/74343 A2 | 10/2001 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/103584 A2 | 12/2003 |

OTHER PUBLICATIONS

Kagy, 2000, Dermatolog. Surg. vol. 26, pp. 577-579.*

Marks, 2001, J. Am. Acad. Dermatol. 2001, vol. 44, pp. 807-813.*

Testerman, et al., "Cytokine Induction by the Immunomodulators Imiquimod and S-27609", *Journal of Leukocyte Biology*, vol. 58, pp. 365-372, Sep. 1995.

Chollet, et al, "Development of a Topically Active Imiquimod Formulation", *Pharmaceutical Development and Technology*, 4(1), pp. 35-43 (1999).

Brassard et al.; "Interferon-α as an immunotherapeutic protein"; Journal of Leukocyte Biology; vol. 71; Apr. 2002; pp. 565-581.

Izumi et al.; "1 *H*-imidazo[4,5-*c*]quinoline Derivatives as Novel Potent TNF-α Suppressors: Synthesis and Structure-Activity Relationship of 1-, 2-and 4-Substituted 1*H*-Imidazo[4,5-*c*]quinolines or 1*H*-imidazo[4,5-*c*]pyridines"; *Bioorganic and Medicinal Chemistry*, vol. 11, pp. 2541-2550 (2003).

Beutner et al.; "Therapeutic response to basal cell carcinoma to the immune response modifier imiquimod 5% cream"; J. Am. Acad Dermatol; vol. 41, No. 6, Dec. 1999; pp. 1002-1007.

Gelsse et al.; "Imiquimod 5% cream for the treatment of superficial basal cell carcinoma: A double-blind, randomized, vehicle-controlled study"; J. Am. Acad. Dermatol; vol. 47, No. 3, Sep. 2002; pp. 390-398.

Marks et al.; "Imiquimod 5% cream in the treatment of superficial basal cell carcinoma: Results of a multicenter 6-week dose-response trial"; J. Am. Acad. Dermatol; vol. 44; No. 5; May 2001; pp: 807-813.

Shumach et al; "Efficacy of Topical 5% Imiquimod Cream for the Treatment of Nodular Basal Cell Carcinoma—Comparison of Dosing Regimens"; Arch Dermatol; vol. 13B; Sep. 2002; pp. 1165-1171.

Starry et al.; "Imiquimod 5% cream for the treatment of superficial and nodular basal cell carcinoma: randomized studies comparing low-frequency dosing with and without occlusion"; British Journal of Dermatology; 2002; 147; pp. 1227-1236.

Marks et al. (J. Am. Acad. Dermatol. 2001; 44: 807-813).

Beutner et al. (J. Am. Acad. Dermatol. 1999; 41: 1002-1007).

Kagy et al. (Dermatol. Surg. 2000; 26: 577-579).

AldaraTM (FDA, Labeling Revision 2001).

* cited by examiner

TREATMENT FOR BASAL CELL CARCINOMA

CROSS-REFERENCES TO RELATED APPLICATIONS

This application is a continuation of U.S. Ser. No. 12/798,356, filed Apr. 2, 2010, now abandoned, which is a continuation of U.S. Ser. No. 12/008,961, filed Jan. 15, 2008, now U.S. Pat. No. 7,696,159, issued Apr. 13, 2010, which is a continuation of U.S. Ser. No. 10/808,004, filed Mar. 24, 2004, now abandoned, which claims priority to U.S. Provisional Application Ser. No. 60/457,265, filed Mar. 25, 2003, the disclosures of all of which are incorporated herein by reference.

BACKGROUND

Basal cell carcinoma (BCC) is the most common form of skin cancer and the most common form of cancer of any type in the United States. It develops in the basal germinative cell layer of the epidermis, often on sun-exposed areas of the skin. Although BCC rarely spreads (i.e., metastasizes) to other parts of the body, it can be very destructive and disfiguring. BCC may cause local tissue destruction that may lead to disfigurement or functional impairment of surrounding non-cancerous tissue. Disfigurement may be a particular concern of BCC patients because many BCC tumors occur on the sun-exposed—and, therefore, also typically otherwise exposed—skin of the head and neck. Larger tumors, tumors that have been present for long periods of time, and tumors that have recurred after initial therapy may be biologically more aggressive and especially difficult to cure. While the mortality rate of BCC is relatively low, its increasing incidence and prolonged morbidity means that the disease can be very costly to treat.

A wide variety of surgical and non-surgical therapies are available for BCC. Nonsurgical therapies include radiation therapy, chemotherapy, and immunotherapy. These therapies can be useful for definitive treatment of primary tumors and some recurrent BCC tumors and for relieving symptoms associated with inoperable tumors. However, some of these therapies also can have significant unpleasant side effects. Side effects of radiation therapy and certain chemotherapies are well documented. One form of immunotherapy involves intralesional injections of interferon. While interferon therapy can be effective against BCC, the multiple intralesional injections can require several clinic visits per week for many weeks. Also, many patients can be anxious or otherwise uncomfortable receiving injections. Thus, interferon therapy can result in significant patient inconvenience and discomfort.

Interferon therapy also is connected with several side effects such as, for example, flu-like symptoms such as fever, chills, aches, drowsiness and nausea; a reduction in the number of white blood cells; a reduction in the number of red blood cells (anemia); a reduction in the number of platelets in the blood, which may give rise to nosebleeds, for example; thinning hair; liver problems; and heart problems.

Surgical therapies include excision, curettage and electrosurgery, cryosurgery, Mohs micrographic surgery, and laser surgery. Excision is useful for both primary and recurrent tumors and has the advantage of allowing for histological assessment of surgical margins. Curettage and electrosurgery involves alternately removing soft tumor tissue with a curette and then destroying an extra margin of tissue by electrodesiccation, electrocautery, or electrocoagulation. The procedure may be repeated as necessary. Cryosurgery involves freezing the tumor to a temperature that kills the cells of the tumor. The dead tumor cells can be removed by, for example, curettage. Mohs micrographic surgery (MMS) involves a surgeon using a microscope to improve identify the margin of the tumor more accurately and more precisely than is possible by unaided visual inspection. MMS can increase the likelihood that the entire tumor is removed and minimize the amount of normal tissue that is removed. Laser surgery involves using a laser to vaporize tumor cells. Alternatively, the laser may be used in lieu of a scalpel blade for excisional surgery.

SUMMARY

It has been found that immune response modifier ("IRM") compounds can provide effective therapeutic treatment for BCC. Accordingly, the present invention provides a method of treating basal cell carcinoma in a subject. Generally, the method includes administering to the subject an amount of an IRM compound effective for treating basal cell carcinoma, wherein the IRM compound is administered in a treatment cycle that includes at least two consecutive days in which the IRM compound is administered and at least one day in which the IRM compound is not administered.

In some embodiments, the treatment cycle includes five days in which the IRM compound is administered and two days in which the IRM compound is not administered.

In some embodiments, the treatment of BCC includes at least six treatment cycles.

Various other features and advantages of the invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1:
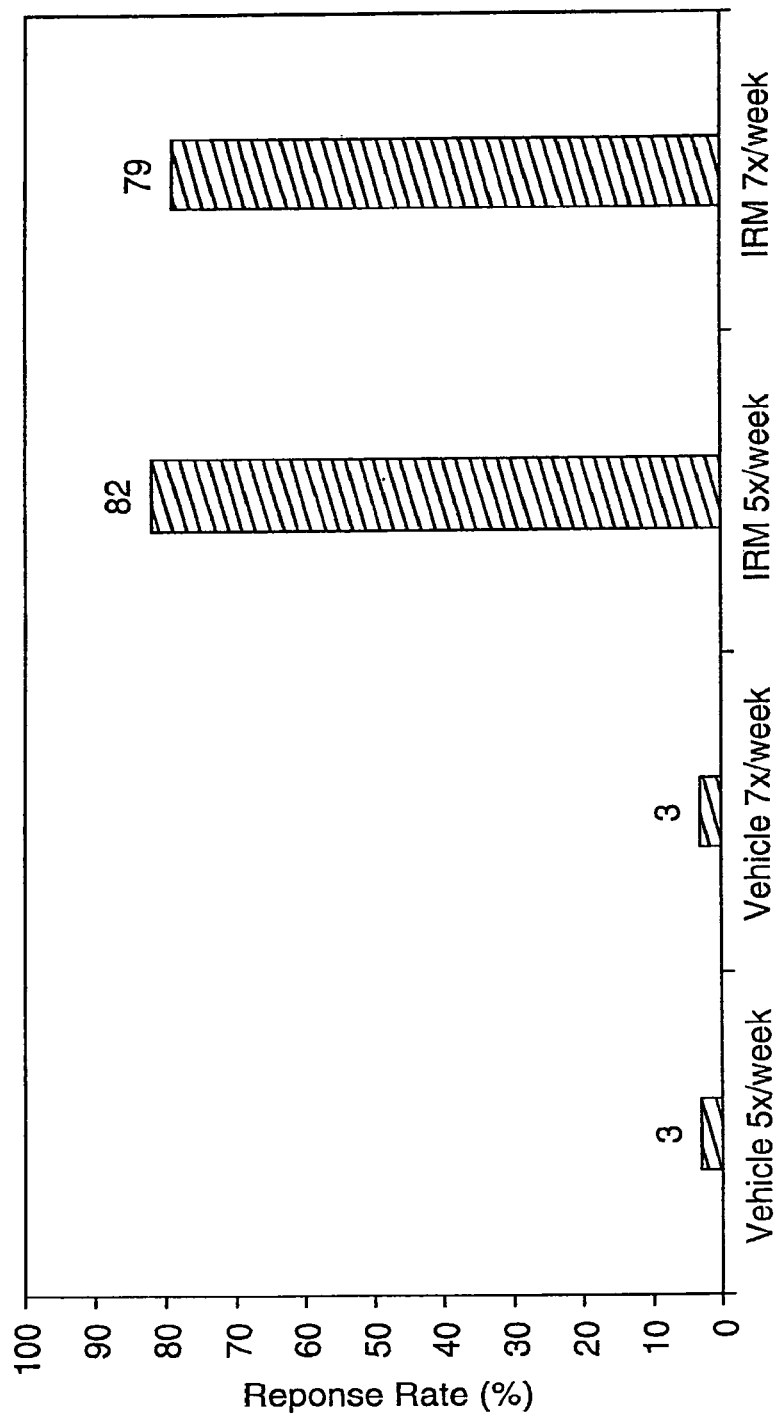
FIG. 1 is a bar graph summarizing data that demonstrate the efficacy of one embodiment of the method of the invention.

Immune response modifiers ("IRMs") include compounds that possess potent immunomodulating activity such as, for example, antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 4,988,815;

5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,541,485; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; European Patent 0 394 026; U.S. Patent Application Publication Nos. 2002/0016332; 2002/0055517; 2002/0110840; 2003/0133913; 2003/0199538; and 2004/0014779; and International Patent Publication Nos. WO 01/74343; WO 02/46749 WO 02/102377; WO 03/020889; WO 03/043572; WO 03/045391; and WO 03/103584.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08595), and certain 3-β-D-ribofuranosylthiazolo[4,5-d]pyrimidine derivatives (such as those described in U.S. Patent Application Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO 00/75304.

Other IRMs include biological molecules such as aminoalkyl glucosaminide phosphates (AGPs) and are described, for example, in U.S. Pat. Nos. 6,113,918; 6,303,347; 6,525,028; and 6,649,172.

By stimulating certain aspects of the immune system, as well as suppressing other aspects (see, e.g., U.S. Pat. Nos. 6,039,969 and 6,200,592), certain IRMs may be used to treat many diseases and conditions. For example, some IRMs may be useful for treating viral diseases, neoplasias, fungal diseases, neoplastic diseases, parasitic diseases, atopic diseases, and opportunistic infections and tumors that occur after suppression of cell-mediated immunity. Certain IRMs may be useful for promoting healing of wounds and post-surgical scars.

Certain formulations of imiquimod, as small molecule IRM compound, have been shown to be useful for the therapeutic treatment of certain cancerous or pre-cancerous lesions (See, e.g., Marks et al., *J. Am. Acad. Dermatol.*, 44(5): 807-813 (2001); Geisse et al., *J. Am. Acad. Dermatol.*, 47(3): 390-398 (2002); Shumack et al., *Arch. Dermatol.*, 138: 1163-1171 (2002); and U.S. Patent Application Publication No. 2003/0199538).

The present invention provides a method of treating basal cell carcinoma using IRMs generally and imiquimod in particular. Generally, the method includes applying an amount of an IRM compound effective for treating basal cell carcinoma, wherein the IRM compound is administered in a treatment cycle that includes at least two consecutive days in which the IRM compound is administered and at least one day in which the IRM compound is not administered.

The particular embodiment of the invention selected for treating basal cell carcinoma can depend, at least in part, on factors relating to the tumor, the patient, or both. Tumor-related variables may include, for example, type, size, shape, histological character, growth character, location, and the like. For example, variables may include whether the tumor is primary or recurrent; greater than a particular size; its duration, growth rate, or both; whether the tumor has indistinct margins, an aggressive histological pattern, or both; and certain anatomic locations. High risk histological patterns include infiltrative/desmoplastic, severe squamous metaplasia, and basosquamous. High-risk locations may include the nose, eyelids, ears, medial canthus, nasolabial fold, scalp, lip, fingers, toes, and genitals. Patient-related variables may include age, medical status, psychological factors, and concomitant medications. For example, patients who are immunocompromised may be at greater risk because their tumors may be more likely to demonstrate very aggressive behavior.

Any suitable IRM compound may be used to practice of the invention. In some embodiments, suitable IRM compounds include but are not limited to the small molecule IRM compounds described above. Suitable small molecule IRM compounds, having a 2-aminopyridine fused to a five membered nitrogen-containing heterocyclic ring, include but are not limited to imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including, but not limited to, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including, but not limited to, amide substituted imidazopyridine amines, sulfonamido substituted imidazopyridine amines, urea substituted imidazopyridine amines, aryl ether substituted imidazopyridine amines, heterocyclic ether substituted imidazopyridine amines, amide ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In certain embodiments, the IRM compound is an imidazoquinoline amine such as, for example, 1-(2-methylpropyl)-1H-imidazo[4,5-c]quinolin-4-amine.

The IRM compound may be provided in a formulation suitable for topical administration. Suitable types of formulations are described, for example, in U.S. Patent Application Publication No. 2003/0199538. The IRM compound may be provided in any suitable form including but not limited to a solution, a suspension, an emulsion, or any form of mixture. The IRM may be delivered in formulation with any pharmaceutically acceptable excipient, carrier, or vehicle. The formulation may be delivered in any conventional dosage form including but not limited to a cream, an ointment, an aerosol formulation, a non-aerosol spray, a gel, a lotion, a tablet, a lozenge, an elixir, and the like. The formulation may further include one or more additives including but not limited to adjuvants, skin penetration enhancers, colorants, fragrances, moisturizers, thickeners, and the like.

The composition of a formulation suitable for practicing the invention will vary according to factors known in the art including but not limited to the physical and chemical nature of the IRM compound, the nature of the carrier, the intended dosing regimen, the state of the subject's immune system (e.g., suppressed, compromised, stimulated), the method of administering the IRM compound, and the species to which the formulation is being administered. Accordingly, it is not practical to set forth generally the composition of a formulation effective for treating BCC for all possible applications. Those of ordinary skill in the art, however, can readily determine an appropriate formulation with due consideration of such factors.

In some embodiments, the invention includes administering the IRM compound to a subject in a formulation of, for example, from about 0.001% to about 10% (unless otherwise indicated, all percentages provided herein are weight/weight with respect to the total formulation) to the subject, although in some embodiments, a suitable formulation may include a concentration of IRM compound that is outside of this range. In certain embodiments, the method includes administering to a subject a formulation that includes from about 0.01% to about 5% IRM compound, for example, a formulation that includes about 5% IRM compound.

An amount of IRM compound effective for treating basal cell carcinoma (BCC) is an amount sufficient to reduce the size or number of BCC lesions, limit or slow the growth of BCC lesions, or both. The precise amount of IRM compound effective for treating BCC will vary according to factors known in the art including, but not limited to, the physical and chemical nature of the particular IRM compound being administered; the physical and chemical nature of the formulation; the size, location, and histological type of BCC being treated; the intended dosing regimen; the state of the subject's immune system (e.g., suppressed, compromised, stimulated); and the method of administering the IRM. Accordingly it is not practical to set forth generally the amount that constitutes an amount of IRM compound effective for treating BCC for all possible applications. Those of ordinary skill in the art, however, can readily determine the appropriate amount with due consideration of such factors.

In some embodiments, the invention includes administering sufficient IRM compound to provide a dose of the IRM compound of, for example, from about 0.001 mg/cm$^2$ to about 100 mg/cm$^2$ to the subject, although in some embodiments the methods may be performed by administering the IRM compound in amounts outside this range. In some of these embodiments, the method includes administering sufficient IRM compound to provide a dose of IRM compound of from about 0.1 mg/cm$^2$ to about 5 mg/cm$^2$ to the subject, for example, a dose of IRM compound of about 0.5 mg/cm$^2$ to about 2 mg/cm$^2$.

The dosing regimen may depend at least in part on many factors known in the art including but not limited to the physical and chemical nature of the IRM compound being administered; the physical and chemical nature of the formulation; the size, location, and histological type of the BCC being treated; the amount of IRM compound being administered; the state of the subject's immune system (e.g., suppressed, compromised, stimulated); and the method of administering the IRM compound. Accordingly, it is not practical to set forth generally the dosing regimen effective for treating basal cell carcinoma for all possible applications. Those of ordinary skill in the art, however, can readily determine an appropriate dosing regimen with due consideration of such factors.

An IRM compound can be effective for treating basal cell carcinoma with a treatment regimen that includes administering the IRM compound from about once per week to multiple daily doses (e.g., two doses per day). In certain embodiments of the invention, treatment of BCC includes administering the IRM compound according to a treatment cycle that includes at least two consecutive days in which the IRM compound is administered and at least one day in which the IRM compound is not administered.

As used herein, a treatment cycle is a repeated cyclical pattern of scheduled treatment. A treatment period typically includes a scheduled number of repeated treatment cycles. A treatment cycle may call for a specified number and schedule of days in which treatment is administered (treatment days) as well as a specified number and schedule of days in which no treatment is administered (off days). Thus, a treatment cycle specifically excludes instances in which scheduled treatments are temporarily interrupted and then subsequently resumed, for example, to allow one or more adverse reactions to subside. The schedule may be as specific as necessary for effective treatment. For example, in one embodiment, a treatment cycle includes five consecutive treatment days and two consecutive off days per week. In other embodiments, however, a treatment cycle may specify the number of treatment days per week (e.g., five) and the number of off days per week (e.g., two), but not specify when the off days must occur relative to the treatment days.

A treatment cycle that includes at least two consecutive treatment days and at least one off day can reduce the likelihood and extent of adverse reactions to the treatment, thereby minimizing the likelihood that treatment will be interrupted for one or more rest periods. A treatment cycle that avoids interrupting treatment can increase the likelihood that the treatment can be completed as initially scheduled. Such treatment cycles also can provide treatment that is nearly as, equally, or even more effective than treatment cycles requiring more frequent administration or greater total dosages.

In certain embodiments, the treatment cycle includes five days of administering the IRM compound and two days in which the IRM compound is not administered. In one particular embodiment, the treatment cycle includes five consecutive days of administering the IRM compound and two consecutive days of not administering the IRM compound. This treatment cycle can provide efficacy equal to or better than, and reduced adverse reactions compared to, treatment cycles that call for administering the same formulation of the IRM compound more frequently or for a greater number of doses within a seven-day cycle.

Treatment periods can range from about two weeks to about 24 weeks. In some embodiments, the treatment period may be a predetermined fixed length of time. For example, the treatment period can be at least about two weeks, at least about four weeks, at least about six weeks, at least about eight weeks, at least about 12 weeks, or at least about 16 weeks, although in some embodiments the methods may be performed by administering the IRM compound for treatment periods outside this range. Alternatively, the treatment period may terminate upon reaching a particular milestone. For example, a treatment period of one embodiment of the method according to the present invention may continue until a lesion being treated is resolved. Evidence that the lesion is resolved may be obtained by any medically acceptable means including but not limited to clinical examination or histological examination.

FIG. 1 summarizes data regarding one measure of efficacy for one embodiment of the invention. Subjects were divided into four treatment groups: (1) placebo cream, once per day, five days per week (Vehicle 5x/week); (2) placebo cream, once per day, seven days per week (Vehicle 7x/week); (3) 5% IRM (imiquimod) cream, once per day for five days per week and two consecutive days without treatment per week (IRM 5x/week); and (4) 5% IRM (imiquimod) cream, once per day, seven days per week (IRM 7x/week).

Subjects received treatment for six weeks, then returned twelve weeks after the end of treatment for a post-treatment visit. At the post-treatment visit, the entire tumor area—including an area up to a 3-4 mm around the pre-treatment tumor margin—was excised. The excised tissue was examined histologically for evidence of BCC. The proportion of subjects who had no histological evidence of BCC in the post-treatment excision taken from the treatment site twelve weeks after the end of treatment were considered complete histological responders. FIG. 1 shows the proportion of complete histological responders in each treatment group. The IRM 5x/week group exhibited the highest proportion of complete histological responders.

Figure 2:
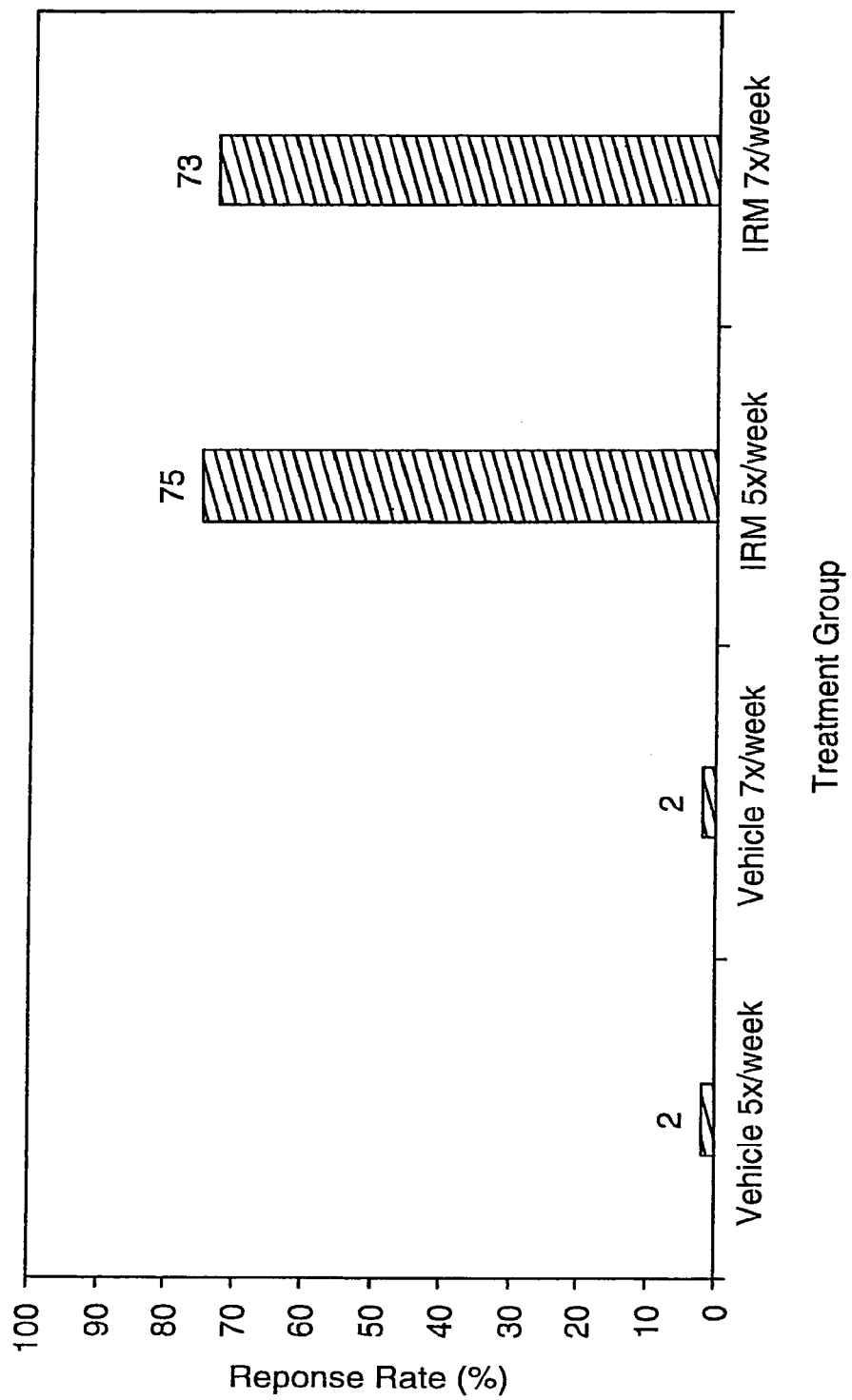
FIG. 2 is a bar graph summarizing data that demonstrate the efficacy of one embodiment of the method of the invention.

FIG. 2 summarizes data regarding a second measure of efficacy for the embodiment of the invention described above. FIG. 2 shows the proportion of composite complete responders in each treatment group. Composite complete responders are those who display both (1) no histological evidence of BCC twelve weeks after the end of treatment, and (2) no clinical evidence of BCC twelve weeks after the end of treatment. The IRM 5x/week treatment group exhibited the highest proportion of composite complete responders.

Figure 3:
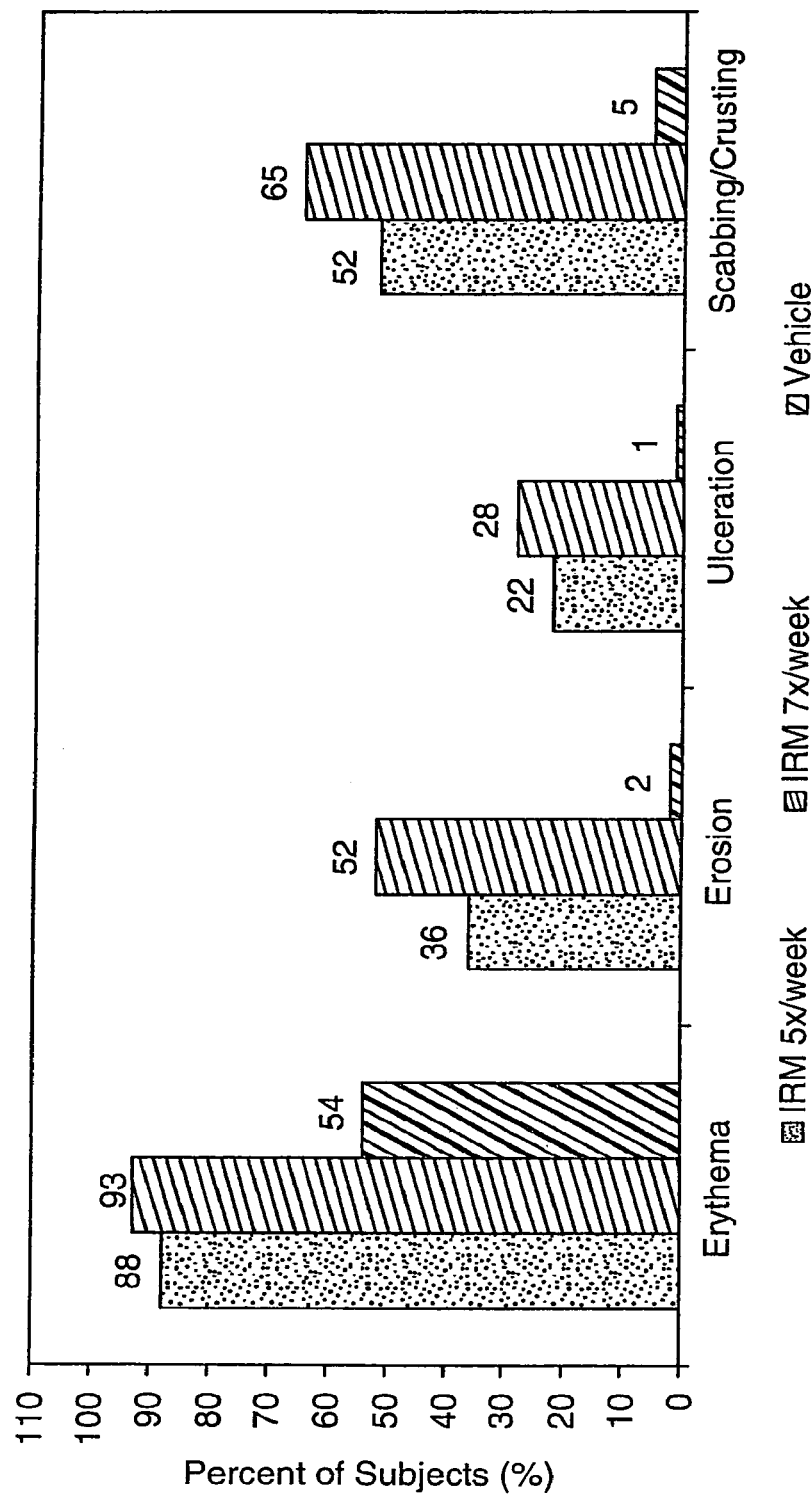
FIG. 3 is a bar graph summarizing data related to the frequency of adverse local skin reactions.

FIG. 3 summarizes a comparison of moderate and severe adverse local skin reactions among the treatment groups (the Vehicle group in FIG. 3 equals the combination of the Vehicle 5x/week group and Vehicle 7x/week group). Subjects completed interval visits 1, 3, and 6 weeks after treatment was initiated and at twelve weeks after the end of treatment. The presence of local skin reactions (i.e., erythema, erosion, ulceration, and scabbing) was assessed at each interval visit and at the 12-weeks post-treatment visit on a four-point scale (0, none; 1, mild; 2, moderate; and 3 severe). Reports of local skin reactions are summarized in FIG. 3, expressed as the percentage of subjects in each treatment group that reported a moderate or sever local skin reaction at any time during the study. The incidence of moderate and severe local skin reactions was less in the IRM 5x/week treatment group than in the IRM 7x/week treatment group for each local skin reaction shown in FIG. 3.

In some embodiments, administering the IRM compound involves topical application of a formulation that contains IRM compound. The formulation may be topically applied to a treatment area located on the skin of the subject. The treatment area can include an area of the skin that includes a BCC lesion. The treatment area also may, in some embodiments, include an area of skin surrounding the BCC lesion (i.e., extramarginal skin—skin beyond the margin of the lesion).

The treatment area may include extramarginal skin that is uniform or irregular in shape, and may be of uniform or irregular width around the margin of the lesion. In some embodiments, the method includes application of a formulation that includes an IRM compound to a treatment area that includes a BCC lesion and skin from about 0.5 cm to about 5.0 cm beyond the margin of the lesion, for example, 1.0 cm beyond the margin of the lesion.

The IRM compound may be left on the treatment area for any suitable amount of time. The precise duration of time that a particular application of the IRM compound should remain on the treatment site may vary according to, for example, the dose of the IRM compound being administered, the state of the subject's immune system, the size and character of the tumor, the extent to which the subject has experienced an adverse reaction, and the like. In some embodiments, the method includes ensuring that the IRM compound is applied to the treatment site for from about one hour to about 48 hours, although certain embodiments of the invention may be practiced by administering IRM compound to a subject for periods outside this range. In certain embodiments, the IRM compound is applied for from about two hours to about 24 hours. In other embodiments, the IRM compound is applied for from about six hours to about twelve hours, for example, about eight hours.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

The IRM compound was provided in a 5% cream in a formulation shown in Table 1, on a percentage weight-by-weight basis. The IRM compound used to prepare the formulation was imiquimod, 1-(2-methylpropyl)-1H-imidazo[4,5-c]quinolin-4-amine. Imiquimod and methods of synthesizing imiquimod are disclosed in, for example, U.S. Pat. No. 4,689,338.

TABLE 1

| Components | Formulation (% w/w) |
| --- | --- |
| IRM | 5.0 |
| Isostearic Acid | 25.0 |
| Benzyl Alcohol | 2.0 |
| Cetyl Alcohol | 2.2 |
| Stearyl Alcohol | 3.1 |
| White Petrolatum | 3.0 |
| Polysorbate 60 | 3.4 |
| Sorbitan Monostearate | 0.6 |
| Glycerin | 2.0 |
| Methyl Paraben | 0.2 |
| Propyl Paraben | 0.02 |
| Water | 52.98 |
| Xanthan Gum | 0.5 |

The formulation was prepared according to the methods described in U.S. Pat. No. 5,238,944. The final formulation had a pH of 5.1, and a viscosity (cps) of $0.33 \times 10^5$.

Example 1

Volunteer subjects with superficial basal cell carcinoma were randomized to either the 5% imiquimod cream formulation described above or a placebo cream (Vehicle) in one of two treatment regimens: (1) once daily for seven days per week (7×/week), and (2) once daily for five consecutive days per week and no treatment for the remaining two days (5×/week). Subjects in each groups received treatment for six weeks.

Subjects were instructed to administer a single application of cream (Vehicle or 5% imiquimod, as assigned) to a target tumor just prior to normal sleeping hours according to the dosing regimen to which they were assigned. The subjects were instructed to wash the tumor lesion prior to applying the cream, and then rub the cream into the tumor and into extra-marginal skin about 1 cm around the tumor. The subjects were instructed to leave the cream in place for at least eight hours without occlusion.

Subjects completed interval visits 1, 3, and 6 weeks after treatment was initiated and at twelve weeks after the end of treatment. At the 12-weeks post-treatment visit, the treatment area was clinically evaluated and the entire tumor area—an area up to a 3-4 mm around the pre-treatment tumor margin—was excised. The excised tissue was examined histologically for evidence of BCC. FIG. 1 summarizes the results of the histological assessment, expressed as the percentage of subjects in each treatment group that exhibited a complete histological response, i.e., the proportion of subjects who had no histological evidence of BCC in the post-treatment excision taken from the treatment site twelve weeks after the end of treatment. FIG. 2 summarizes the results of the composite assessment, expressed as the percentage of subjects having both (a) no clinical evidence of BCC twelve weeks after the end of treatment, and (b) a complete histological response.

The presence of local skin reactions (i.e., erythema, erosion, ulceration, and scabbing) was assessed at each interval visit and at the 12-weeks post-treatment visit. Reports of local skin reactions are summarized in FIG. 3, expressed as the percentage of subjects in each treatment group that reported a given local skin reaction during the study.

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the invention. The scope of the invention is limited only by the claims set forth as follows.

What is claimed is:

1. A method of treating basal cell carcinoma in a subject, the method consisting essentially of administering to the subject an amount of an Immune Response Modifier (IRM) compound effective for treating basal cell carcinoma, wherein administering the IRM compound comprises topically applying the IRM compound to a treatment area that includes a lesion, and wherein the IRM compound is administered in a treatment cycle that comprises five consecutive days in which the IRM compound is administered and at least two consecutive days in which the IRM compound is not.

2. The method of claim 1 wherein the method comprises at least two treatment cycles.

3. The method of claim 2 wherein the method comprises at least six treatment cycles.

4. The method of claim 1 wherein administering the IRM compound comprises applying one dose of the IRM compound per day.

5. The method of claim 1 wherein the IRM compound is applied in a formulation that comprises from about 1% to about 10% IRM compound.

6. The method of claim 5 wherein the formulation comprises about 5% IRM compound.

7. The method of claim 5 wherein the formulation is applied to the treatment area for from about two hours to about 24 hours.

8. The method of claim 7 wherein the formulation is applied to the treatment area for from about six hours to about twelve hours.

9. The method of claim 5 wherein the formulation is applied to the treatment area for about eight hours.

10. The method of claim 1 wherein the treatment area further comprises skin at least 0.5 cm beyond the margin of the lesion.

11. The method of claim 1 wherein the IRM compound is a 2-aminopyridine fused to a five membered nitrogen-containing heterocyclic ring.

12. The method of claim 1 wherein the IRM compound is imiquimod.

* * * * *